US00PP12341P2

(12) United States Plant Patent
Saeys

(10) Patent No.: US PP12,341 P2
(45) Date of Patent: Jan. 8, 2002

(54) EUONYMUS PLANT NAMED 'SUNRISE'

(75) Inventor: Erik Saeys, Oakville (CA)

(73) Assignee: CP (Delaware), Inc., Wilmington, DE (US)

( * ) Notice: Subject to any disclaimer, the term of this patent is extended or adjusted under 35 U.S.C. 154(b) by 3 days.

(21) Appl. No.: 09/611,366

(22) Filed: Jul. 6, 2000

(51) Int. Cl.[7] ..... A01H 5/00
(52) U.S. Cl. ..... Plt./246
(58) Field of Search ..... Plt./246

*Primary Examiner*—Bruce R. Campell
*Assistant Examiner*—Annette H. Para
(74) *Attorney, Agent, or Firm*—Burns, Doane, Swecker & Mathis, L.L.P.

(57) ABSTRACT

A new and distinct variety of *Euonymus fortunei* is provided. The variety forms attractive variegated leaves that are green towards the center and are irregularly bordered with bright golden yellow coloration. Such coloration commonly is retained even if the plants are grown in partial shade. The growth habit is broadly pyramidal. Superior Anthracnose disease resistance is exhibited. The new variety is well suited for growing as a bright ornamental plant.

2 Drawing Sheets

SUMMARY OF THE INVENTION

The new *Euonymus fortunei* plant is believed to be a spontaneous mutation of unknown causation that was discovered while growing among plants of the 'Emerald Charm' variety (U.S. Plant Pat. No. 1,079) at Oakville, Ontario, Canada. Initially I was primarily attracted to the new variety by the distinctive coloration of its foliage and the different growth habit. The new variety subsequently has been studied to confirm its distinctive characteristics.

It was found that the new *Euonymus fortunei* variety of the present invention exhibits the following combination of characteristics:

(a) Forms a broadly pyramidal growth habit, (b) Forms variegated leaves that are green and irregularly bordered with bright golden yellow that commonly possess the ability to retain such coloration even if grown in partial shade, (c) Exhibits superior Anthracnose disease resistance, and (d) Is well suited for growing as attractive ornamentation.

The yellow margins of the leaves are considerably brighter than those of other *Euonymus fortunei* varieties, including 'Gold Tips' (non-patented in the United States), 'Canandale Gold' (non-patented in the United States), and 'Sheridan Gold' (non-patented in the United States). From a distance in the Spring the plant may even be mistaken to be a Forsythia to the casual observer. In addition, the central green coloration of the leaves is considerably darker and provides a greater contrast with bright golden yellow margin coloration. The new variety has proven to be one of the most Anthracnose resistant cultivars that is commercially available today. Its ability to retain a variegated leaf coloration even in partial shade is considered to be unusual for a variegated *Euonymus fortunei.*

The new variety readily can be distinguished from its 'Emerald Charm' parent. More specifically, the new variety forms leaves having bright golden yellow borders, exhibits a broad growth habit unlike the upright columnar growth habit of 'Emerald Charm', and forms flowers unlike 'Emerald Charm'.

The new variety has been asexually reproduced by cuttings at Oakville, Ontario, Canada, and at West Grove, Pa. The characteristics of the new variety have been found to be strictly transmissible from one generation to another following such asexual reproduction.

The new variety of the present invention well meets the needs of the horticultural industry. It can be used to provide attractive ornamentation in the landscape, a specimen plant, foundation planting, ground cover, or be incorporated into mass planting.

The new variety of the present invention has been named 'Sunrise'.

BRIEF DESCRIPTION OF THE PHOTOGRAPHS

The accompanying photographs show as true as it is reasonably possible in color illustrations of this nature, plants and plant parts of the new variety of the present invention. The plants were approximately three years of age and were photographed during midsummer while growing in the landscape at West Grove, Pa.

Figure 1:
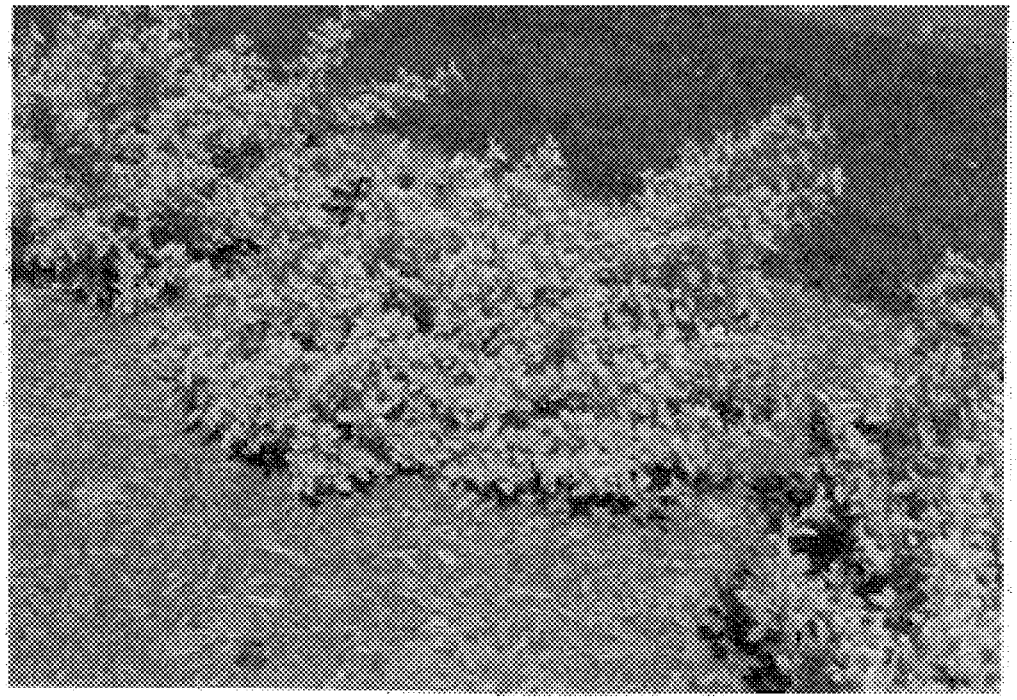
Figure 2:
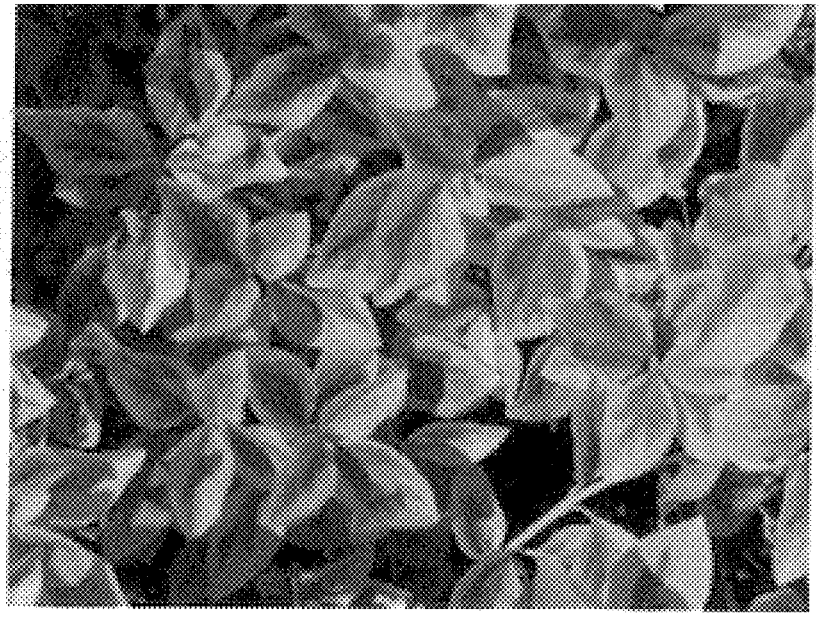

FIG. 1—shows the typical overall growth habit of the plant wherein the width exceeds the height, and FIG. 2—shows a closer view of the foliage during the summer. The green leaves are irregularly margined with bright golden yellow.

Figure 3:
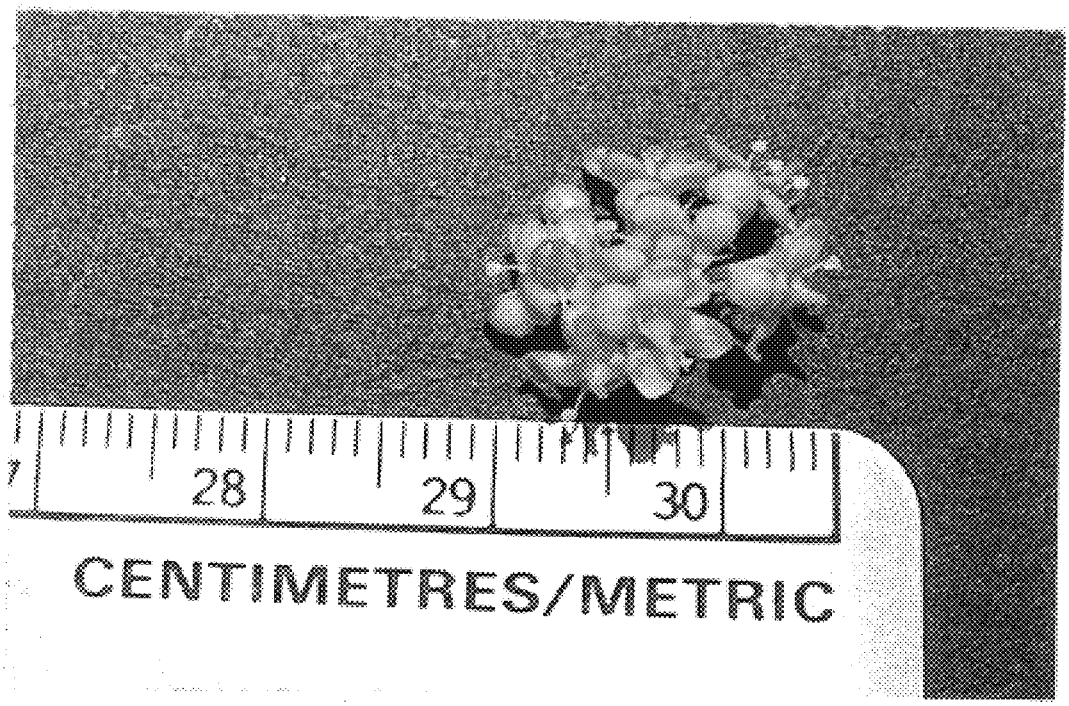

FIG. 3—shows typical flower buds and flowers. Dimensions in centimeters are included at the bottom of the photograph.

DETAILED DESCRIPTION

The chart used in the identification of colors is that of The Royal Horticultural Society, London (R.H.S. Colour Chart). The description is based upon the inspection of plants having an age of approximately three years while growing in containers at West Grove, Pa. Such plants had been asexually reproduced by the use of cuttings.

Botanical classification: *Euonymus fortunei*, cv. 'Sunrise'.

Parentage: Believed to be a spontaneous mutation of unknown causation of the 'Emerald Charm' variety (U.S. Plant Pat. No. 1,079).

Propagation: Holds its distinguishing characteristics well through asexual reproduction by the use of cuttings.

Plant:

*Type.*—Broadleaf evergreen shrub with petioled and opposite leaves.

*Growth habit.*—Compact and generally broadly pyramidal. This can be compared to the upright columnar growth habit of the 'Emerald Charm' variety.

*Growth rate.*—Generally comparable to that of the 'Emerald Charm' variety.

*Height.*—Approximately 2 feet at 5 years and when fully mature.

*Width.*—Approximately 3 feet at 5 years and approximately 4 feet when fully mature.

Foliage characteristics:

*Configuration.*—Slightly variable, mostly obovate with some leaves approaching an elliptic configuration. The base is rounded and the margins are serrate to serrate—crenate.

*Size.*—Approximately 3 to 4 cm in length and approximately 2 to 2.5 cm in width.

*Glossiness.*—Semi-glossy.

*Color.*—Immature Leaves: Yellow is the predominant color. The central portion is a blend of Green Group 137B, 138B and 138D, and the irregularly defined borders are Yellow-Orange Group 14C with flecks of Greyed-Yellow Group 160A. Mature Leaves: Shades of green are the predominant color. The central portion is a blend of Green Group 137A, 137C and 138C, and the irregularly defined borders are Yellow-Orange Group 14C and 14B.

*Petiole.*—Approximately 3 to 5 mm in length.

Flowers:

*Bearing.*—Commonly in clusters of six.

*Buds.*—Yellow-Green Group 154C in coloration, and approximately 2 mm in diameter.

*Petal shape.*—Oval.

*Petal size.*—Approximately 3 mm in length and approximately 2 mm in width.

*Petal texture.*—Generally smooth with the presence of some generally lengthwise grooves.

*Petal number.*—Four per flower.

*Diameter.*—Approximately 15 mm.

*Color.*—Yellow-Green Group 154D on the upper surface and Yellow-Green Group 154C on the under surface.

*Stamen.*—Four in number having heights of approximately 2 mm.

*Pollen.*—None observed to date.

*Fruit and seeds.*—None observed to date.

Hardiness: Can be grown in U.S.D.A. Hardiness Zone Nos. 4 to 8.

Disease resistance: Very good with superior resistance to Anthracnose being exhibited.

I claim:

1. A new and distinct variety of *Euonymus fortunei* plant that exhibits the following combination of characteristics:

(a) Forms a broadly pyramidal growth habit, (b) Forms variegated leaves that are green and irregularly bordered with bright golden yellow that generally possess the ability to retain such coloration even if grown in partial shade, (c) Exhibits superior Anthracnose disease resistance, and (d) Is well suited for growing as attractive ornamentation; substantially as herein shown and described.

* * * * *